US007721897B2

(12) United States Patent
Woolley et al.

(10) Patent No.: US 7,721,897 B2
(45) Date of Patent: May 25, 2010

(54) AUTOMATED SAMPLE COLLECTION APPARATUS

(75) Inventors: Randy P. Woolley, West Valley City, UT (US); Kevin Quapp, Park City, UT (US)

(73) Assignee: Kennecott Utah Copper LLC, South Jordan, UT (US)

( * ) Notice: Subject to any disclaimer, the term of this patent is extended or adjusted under 35 U.S.C. 154(b) by 469 days.

(21) Appl. No.: 11/839,660

(22) Filed: Aug. 16, 2007

(65) Prior Publication Data

US 2009/0044642 A1     Feb. 19, 2009

(51) Int. Cl.
  *B07C 5/36* (2006.01)
  *B07C 5/38* (2006.01)
  *G01N 1/04* (2006.01)

(52) U.S. Cl. ............... 209/695; 209/2; 209/655; 209/656; 209/691; 73/863.91; 73/863.92; 73/864.41; 73/864.43

(58) Field of Classification Search ........... 73/863.91, 73/863.92, 864.41, 864.43, 864.51; 209/2, 209/655, 656, 691, 707
See application file for complete search history.

(56) References Cited

U.S. PATENT DOCUMENTS

| | | | | |
|---|---|---|---|---|
| 2,348,936 A | * | 5/1944 | Sprenger | 453/12 |
| 3,147,839 A | * | 9/1964 | White, Jr. | 194/317 |
| 3,795,252 A | * | 3/1974 | Black | 453/6 |
| 3,897,875 A | * | 8/1975 | Luckett | 209/705 |
| 4,205,743 A | * | 6/1980 | Whitmore | 198/393 |
| 4,418,771 A | * | 12/1983 | Henry et al. | 177/1 |
| 4,467,882 A | * | 8/1984 | Mikami | 177/58 |
| 4,775,353 A | * | 10/1988 | Childers et al. | 453/6 |
| 4,925,002 A | * | 5/1990 | Williams | 198/445 |
| 5,040,657 A | * | 8/1991 | Gunn et al. | 194/317 |
| 5,267,426 A | * | 12/1993 | Davis | 53/154 |
| RE34,934 E | * | 5/1995 | Raterman et al. | 453/10 |
| 5,545,856 A | * | 8/1996 | Stapp et al. | 177/25.18 |
| 5,752,367 A | * | 5/1998 | VerMehren | 53/473 |
| 5,765,335 A | * | 6/1998 | Simionato | 53/154 |
| 5,765,655 A | * | 6/1998 | Tatsuoka | 177/25.18 |
| 6,227,378 B1 | * | 5/2001 | Jones et al. | 209/698 |
| 6,493,605 B1 | * | 12/2002 | Prideaux et al. | 700/240 |
| 2003/0089529 A1 | * | 5/2003 | Komatsu | 177/25.18 |

FOREIGN PATENT DOCUMENTS

FR     2691384 A1 * 11/1993

* cited by examiner

*Primary Examiner*—David A. Rogers
(74) *Attorney, Agent, or Firm*—Whyte Hirschboeck Dudek SC

(57) ABSTRACT

An apparatus and method for collecting, sorting and storing samples from multiple batches of copper cathode is disclosed. Samples are collected at a sampling station and transferred to a collection container. The samples are then transferred to a sorting container by way of chutes forming a continuous path from the collection container to the sorting container. The sorting container is affixed on the top surface of an automated carousel having a plurality of sorting containers for sorting samples from multiple batches. Samples in the sorting containers are recovered into storage containers through an access door panel and a funnel placed beneath the access door.

16 Claims, 6 Drawing Sheets

AUTOMATED SAMPLE COLLECTION APPARATUS

FIELD OF THE INVENTION

The present invention relates generally to sampling. In one aspect, the invention relates to an apparatus for collecting samples from a production line while in another aspect, the invention relates to an automated apparatus comprising a carousel for the continuous collection of samples. In still another aspect, the invention relates to an automated method of collecting samples, particularly copper cathode samples.

BACKGROUND OF THE INVENTION

Copper cathode is produced by an electrolytic refining process of dissolving copper from copper anodes that are about 98-99% copper by weight. By virtue of placing the impure copper anode into an electrolyte solution under the influence of a pre-determined current density, copper ions from the anode migrate to a cathode which is normally made of a stainless steel starter sheet. Such a migration of the copper ions selectively plates the dissolved copper in "pure" form onto the stainless steel cathode, the thickness of which increases as the electrolytic refining process proceeds. Furthermore, metals that are more electropositive than copper tend to remain insoluble and separate out as impurities collecting at the bottom of the cell as a slime. The deposited copper on the cathode is approximately 99.99% pure copper. However, due to a variety of factors, such as variation in current density, minor quantities of impurities including, for example, bismuth, arsenic and antimony, can be trapped in the deposited copper.

The presence of such impurities can be highly undesirable, especially in specialty applications like manufacturing of integrated circuits where the effectiveness of the circuits is sensitive to any increase in impurity. Therefore, samples are frequently taken for conducting purity analysis of the manufactured copper cathode. The typical sample is a quarter-size disk of ½ to one inch in thickness punched from a copper cathode sheet. The sample is collected in a bucket or similar container. However, the operation of the production line is often disrupted either to empty the collection bucket between different batches of copper cathode to prevent mixing of samples from different batches or simply to replace a full bucket with an empty bucket. Such disruptions can accumulate over extended periods of time to the extent that a full day's production can be lost over the period of a month. This, in turn, can result in significant monetary losses to the manufacturer. Moreover, present sampling techniques require constant supervision of the sampling process to replace, sort, store and track the samples and buckets. Productivity can further be limited by the size of the sampling regime, i.e., the more cathode copper sampled, the more production disruptions and the more supervision of the sampling operation is required.

In consideration of the above problems, manufacturers of copper cathode have an interest in a system that continuously collects, sorts and stores copper cathode samples without disrupting the progress of the production line. Advantageous of such a system would include minimum supervision; the collection, sorting and storage of samples from different batches; and infrequent and easy maintenance of the equipment.

SUMMARY OF THE INVENTION

According to this invention, an apparatus for collecting, sorting and storing samples, particularly copper cathode samples, comprises:
  A. A carousel comprising a plurality of sorting containers;
  B. Means for rotating the carousel;
  C. Means for transferring samples from a sample station located apart from the carousel to the sorting containers; and
  D. Means for transferring samples from the sorting containers to storage containers located apart from the carousel.

In one embodiment of the invention, the carousel is automated and comprises multiple sorting containers affixed to its top surface by way of a pivot rod assembly such that the sorting containers can pivot freely about the assembly. The carousel is capable of rotation in either a clockwise or counter-clockwise direction, and rotation is imparted by means of an electric motor, e.g., a servo-electric motor, in a power transfer engagement with a gearbox which in turn is in a rotational engagement with a fastening plate attached to the top surface of the carousel.

In another embodiment of this invention, the means for transferring samples from the sampling station to the sorting containers comprises a collection container for collecting and temporarily storing samples, and first and second chutes for transferring samples from the collection container to the sorting containers mounted on the carousel.

In still another embodiment of this invention, the means for transferring samples from the sorting containers to the storage containers comprises a handle on the bucket and a funnel located beneath the carousel such that the buckets can be rotated about the pivot rod so as to tip the bucket in a manner that the samples pour from the bucket through the funnel into storage containers that can be labeled and transferred to quality control for purity testing.

In yet another embodiment, the apparatus for collecting, sorting and storing copper cathode samples comprises (i) an operator or control station comprising an operator control panel to manage the flow of the samples from the sampling station to the sorting containers, and from the sorting containers to the storage containers, and (ii) an access door or panel assembly to separate the carousel from the operating environment generally, and the operator specifically. The access door assembly comprises a magnetically locked access door through which an operator or other person can obtain access to the sorting buckets to retrieve the collected samples. The access panel and door are safety features to guard against unwanted and/or accidental contact with the carousel.

In another embodiment of this invention, samples, particularly copper cathode samples, are collected, sorted and stored by a process comprising:
  A. Collecting samples at a sampling station and transferring the collected samples to a collection container;
  B. Transferring the samples from the collection container to a sorting container through first and second chutes;
  C. Transferring the samples from the sorting container to a storage container.

In one embodiment of the invention, samples are taken from copper cathode sheets as they move through a production line, and the samples collected in the collection container. Subsequently, by way of a trap door, the contents of the collection container are dumped into the first chute and transferred through a second chute through the action of gravity, optionally with an assist from a vibrator attached to one or both of the first and second chutes, to the sorting containers positioned on the carousel.

In another embodiment, the sorting containers are affixed on the top surface of an automated rotating carousel. The carousel is rotated such that a sorting container is positioned beneath the second chute for receiving samples. After collecting the samples, the sorting container is moved from beneath the second chute to a position such that the samples can be transferred through a funnel into a storage container positioned beneath and apart from the carousel.

Although the present invention is described in the context of collecting copper cathode samples, the invention has utility in numerous other applications such as collecting, sorting and storing samples from other metals (e.g., copper anode, nickel, the precious metals, etc.), manufactured goods (e.g., any mass produced item), fungible goods (e.g., minerals, grains, etc.) and others in which the quality of a large quantity of goods is tested by a sampling regime.

BRIEF DESCRIPTION OF THE DRAWINGS

Various embodiments of the invention are described in the following drawings in which like numerals are employed to designate like parts. Although items of equipment such as valves, fittings, fasteners, sensors and the like have been omitted so as to simply the description, those skilled in the art will recognize that such conventional equipment can be employed as desired.

DESCRIPTION OF THE PREFERRED EMBODIMENT

"Sampling" and like terms means selection and/or removal of one or more representative items or parts of an item, i.e., a sample, from a population of interest such that the selected/removed item or part can be analyzed.

"Assembly" and like terms means a group of parts that fit together to form a self-contained unit and/or independent apparatus that can be used independently or in conjunction with other equipment to perform one or more functions.

"Automated" and like terms mean acting or operating in a manner essentially independent of direct, external human influence or control.

"Longitudinal" and like terms means movement/alignment along the major (lengthwise) axis. In the context of copper cathode sampling, the major axis is the axis or direction along which the copper cathode enters and exits the sampling station.

"Latitudinal" and like terms means movement/alignment along the minor (widthwise) axis. In the context of copper cathode sampling, the minor axis is the axis or direction transverse to that along which the copper cathode enters and exits the sampling station.

Figure 1:
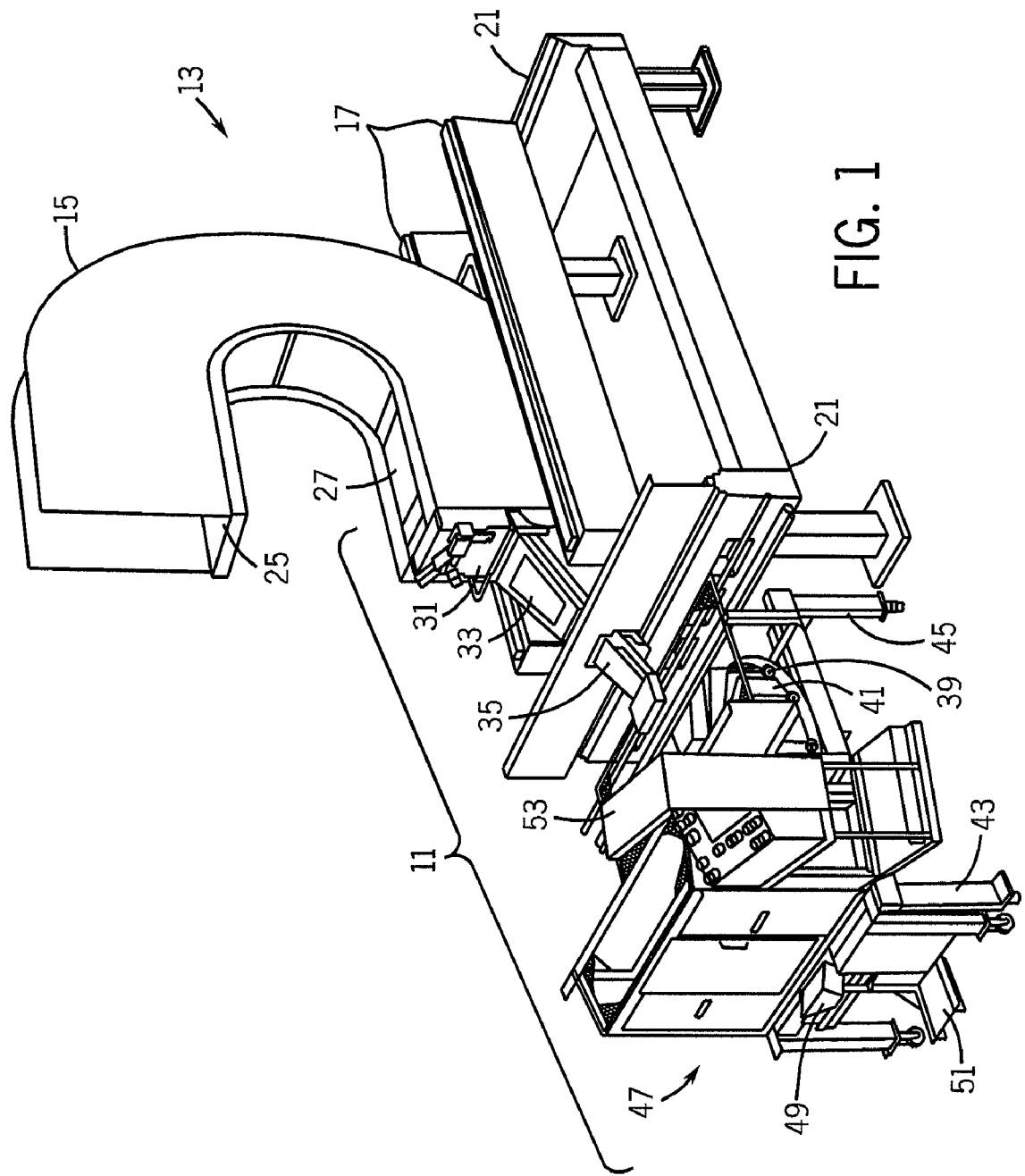
FIG. 1 is a perspective side view of an exemplary automated sample collection apparatus positioned adjacent to a copper cathode sampling station.

Referring to FIG. 1, a perspective side view of automated sample collection apparatus 11 in combination with a copper cathode sampling station is shown in at least some embodiments of the present invention. Copper deposited on a stainless steel cathode starter sheet during the electrolytic refining process of manufacturing copper cathodes from copper anodes is stripped from the start sheet by a cathode stripping device (not shown). The copper cathode (not shown) is then ferried to and through copper cathode sampling station 13 on a conveyor (not shown) for removal of one or more samples for subsequent testing or measurement of copper purity (which typically should be 99.99% or better pure copper). The cathodes are ferried to and move through the sampling station in a horizontal (flat) position relative to the floor upon which the apparatus rests. The samples can be of any size and shape, and are typically in the shape of a disk with a diameter of about 1 inch and a thickness of about ½ to 1 inch. The sampling protocol or regime, i.e., the number of copper cathodes in any given batch from which a sample is taken, the number of samples taken from any given copper cathode, etc., can vary widely.

Sampling station 13 comprises frame 15 in the shape of an inverted C that is mounted atop a first pair of rails 17 which in turn are mounted atop a second pair of rails 21. Rails 17 allow movement of frame 15 in the latitudinal direction, and rails 21 allow movement of frame 15 in the longitudinal direction, both directions relative to the conveyor (not shown) that ferries cathodes to and through the station for sampling. Typically, frame 15 moves in only one direction at a time but those skilled in the art will recognize that the rails and their operation can be configured to allow frame 15 to experience universal direction.

In operation copper cathodes (typically in the shape of eared rectangles of approximately 39 inches by 40 inches by 1 inch and weighing about 300 pounds) move into the channel formed by the two arms of the inverted C. Typically, the cathode is in a flat or horizontal position relative to the floor upon which sampling station 13 rests. At outer end 25 of the top arm of the inverted C is positioned a punch (not shown) capable of cutting a disk shaped sample of about 1 inch in diameter from the copper cathode. Positioned opposite the punch at outer end 27 of the bottom arm of the inverted C is a die (also not shown) in the shape and size such that it can receive the punch and through which the sample can pass. As a copper cathode moves through the channel formed by the arms of the inverted C frame, the cathode stops for a sufficient length of time, e.g., a few seconds, to allow the punch to cut a sample and push the sample through the die into collection container 31. The punch is then retracted to allow the cathode to move out of the channel and to allow another cathode to enter the channel.

Figure 2A:
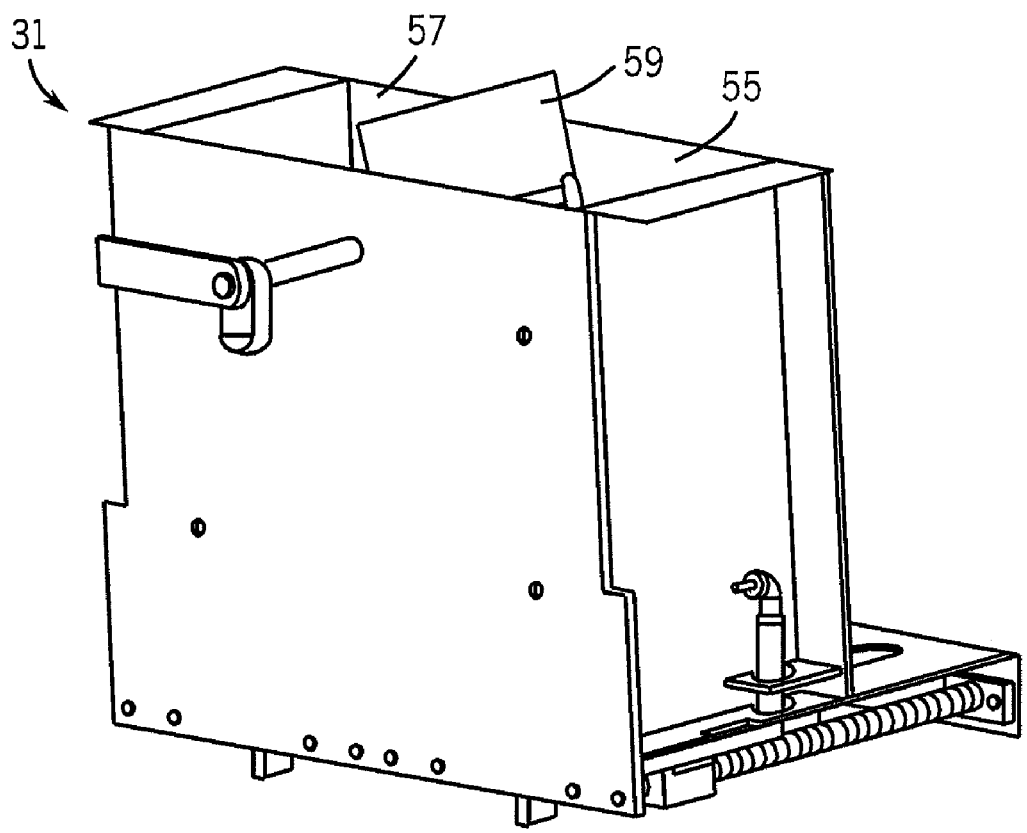
FIG. 2A is a perspective side view of the collection container that forms a part of the automated sample collection apparatus of FIG. 1.
Figure 2B:
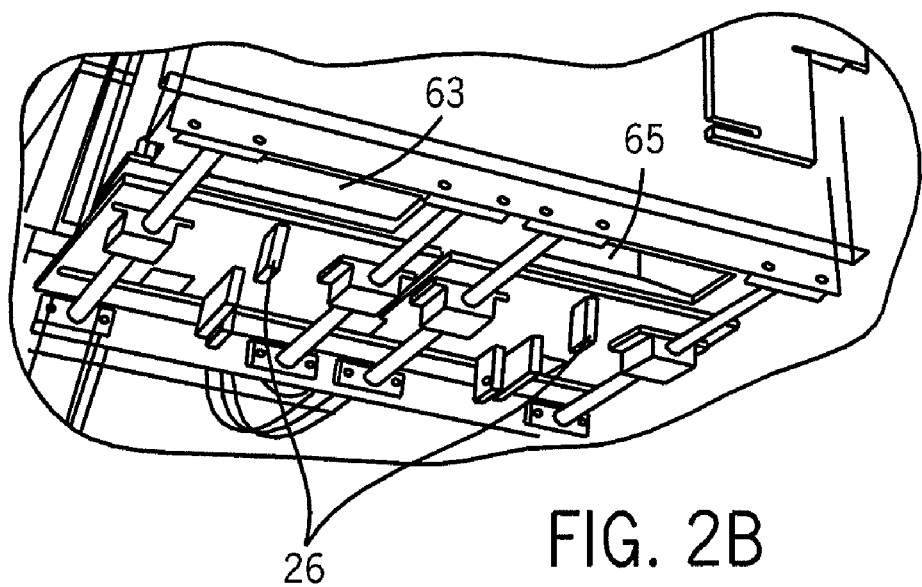
FIG. 2B is a bottom perspective showing the sliding trap door arrangement that forms a part of the bottom of the collection container of FIG. 2A.

Positioned beneath the die and attached to the sampling station 13 is collection container 31. Referring to FIGS. 2A and 2B in conjunction with FIG. 1, collection container 31 is essentially an open box (without a top cover) divided into two chambers, namely, first chamber 55 and second chamber 57, by diverter plate 59 of FIG. 2A. Typically, the chambers are of equal volume, but they can also be of unequal volume. Diverter plate 59, also known as a flop gate, extends from the top of collection container 31 to prevent samples from mixing between chambers 55 and 57. Although in this embodiment only one diverter plate is shown, in other embodiments two or more diverter plates can be used to divide the collection container into three or more chambers of equal or unequal volume. Collection container 31 and its chambers 55 and 57 are sized to the number of samples required/collected per sampling batch. In one embodiment of the invention, each chamber is sized to accommodate approximately 300 samples that are in the shape of a disk with a 1-inch diameter and a ½ to 1 inch thickness.

By dividing collection container 31 into first and second chambers 55 and 57, continuous collection of copper cathode samples is possible without interrupting the continuous operation of the copper cathode production line. While collecting samples in one chamber, samples previously collected and held in the other chamber can be transferred to the carousel for sorting and eventual storage. The emptied chamber can then be repositioned to collect a new batch of samples while the other chamber is emptied of its samples. Since collection chamber 31 is attached to frame 15, it moves with frame 15. When one chamber is full or has collected all the samples necessary from a given batch of copper cathode, the station can be moved (usually left or right in a longitudinal direction) by means of the rails (usually along rails 21) to another position so that passage of copper cathode through it can continue without disruption.

For transferring sample contents from collection container 31 to first chute 33, the bottom of the collection container is equipped with trapdoors 63 and 65. As shown in FIG. 2B, trapdoors 63 and 65 are positioned beneath the first and second chambers 55 and 57, respectively. Each trap door is mounted on a spring loaded linear bearing system (by means well known in the art). The springs assist in keeping trap doors 63 and 65 closed during sample collection and in opening the doors to dump the samples from the chamber into first chute 33. In a preferred embodiment each trapdoor is a sliding door which is moved to one side or another and operated independently of each other. Additionally and preferably, to prevent the contents of the two chambers of the collection container 31 from mixing, only one of the sliding trap doors 63 or 65 can be actuated at any time. Nonetheless, in other embodiments, trap doors 63 and 65 can be of any design, e.g., rotatable, hinged, etc., and can be actuated independently or simultaneously with each other depending upon the requirements of the sampling regime.

Figure 3A:
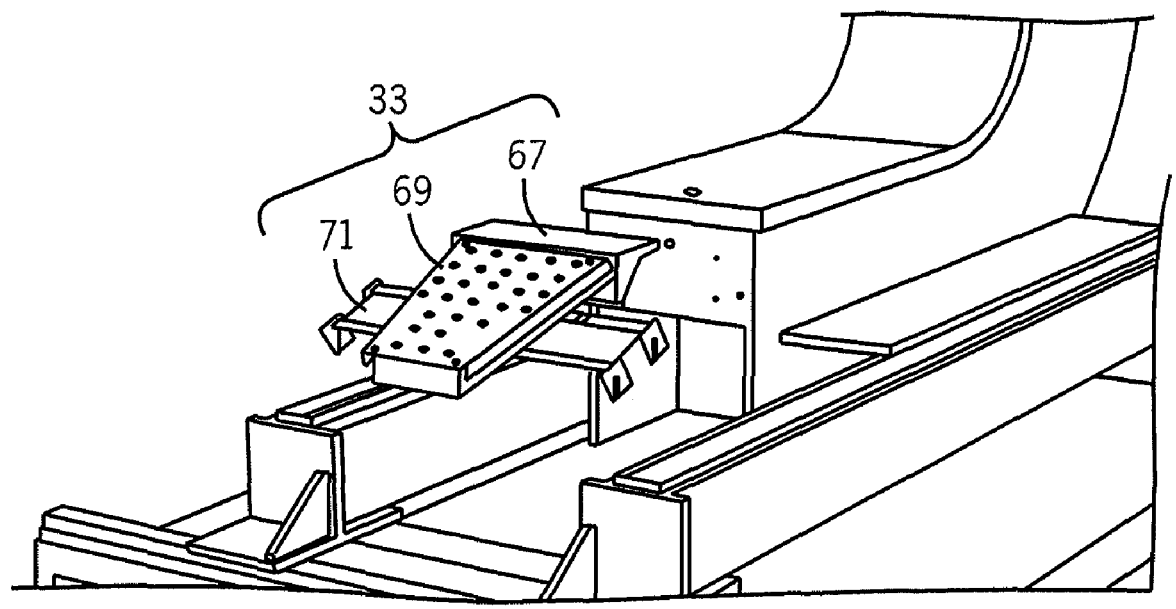
FIG. 3A is a perspective side view of the first chute that forms a part of the automated sample collection apparatus of FIG. 1 and provides a passage way between the collection container of FIG. 2A and the second chute of FIG. 4.
Figure 3B:
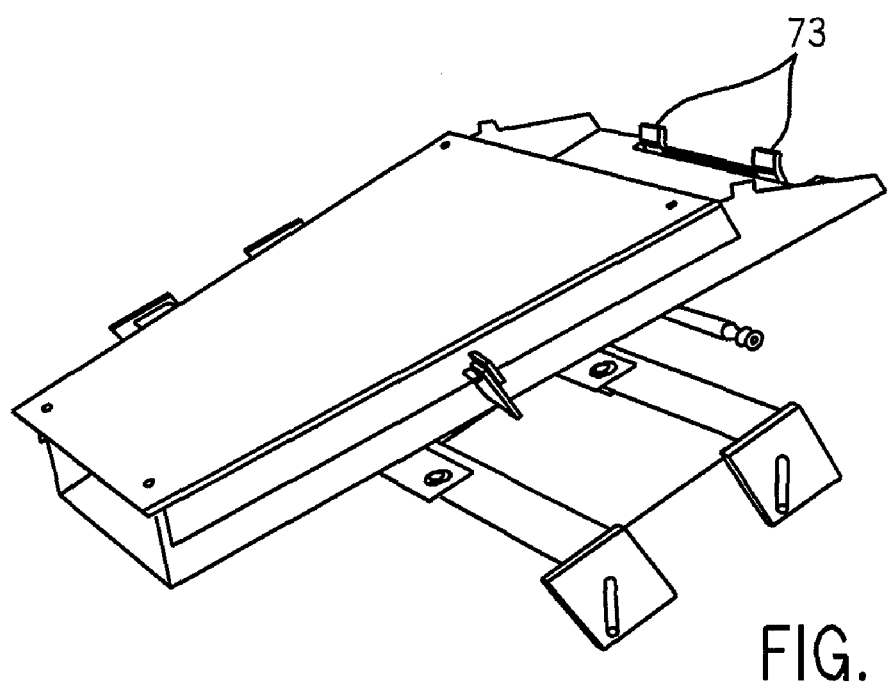
FIG. 3B is a perspective side view of the first chute of FIG. 3A that shows the sliding trap door selectors for the collection container of FIG. 2B.
Figure 4:
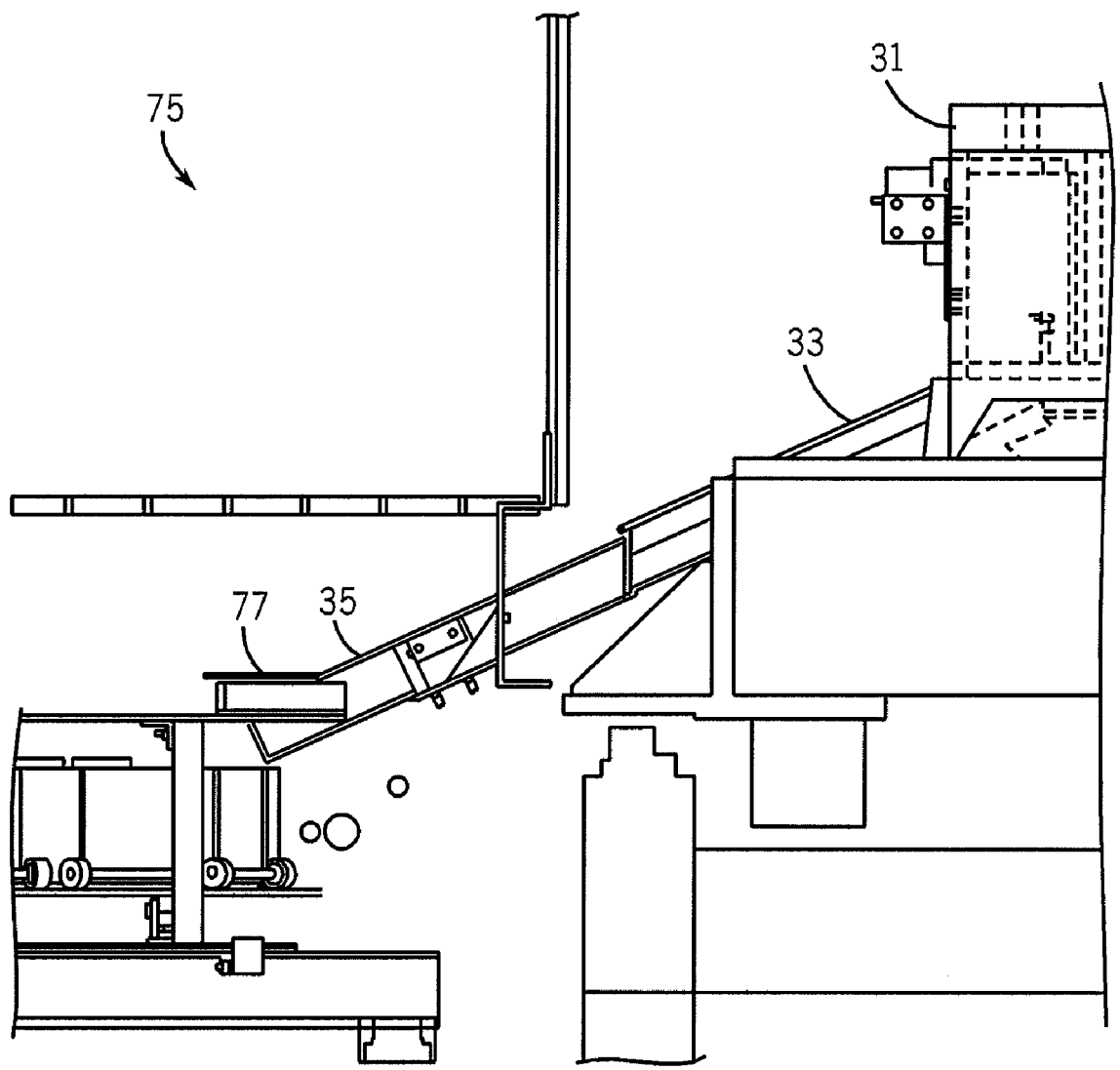
FIG. 4 is a side view perspective of the second chute that forms a part of the automated sample collection apparatus of FIG. 1, and which illustrates its position between the first chute and the sorting containers of FIGS. 5A and 5B.
Figure 5A:
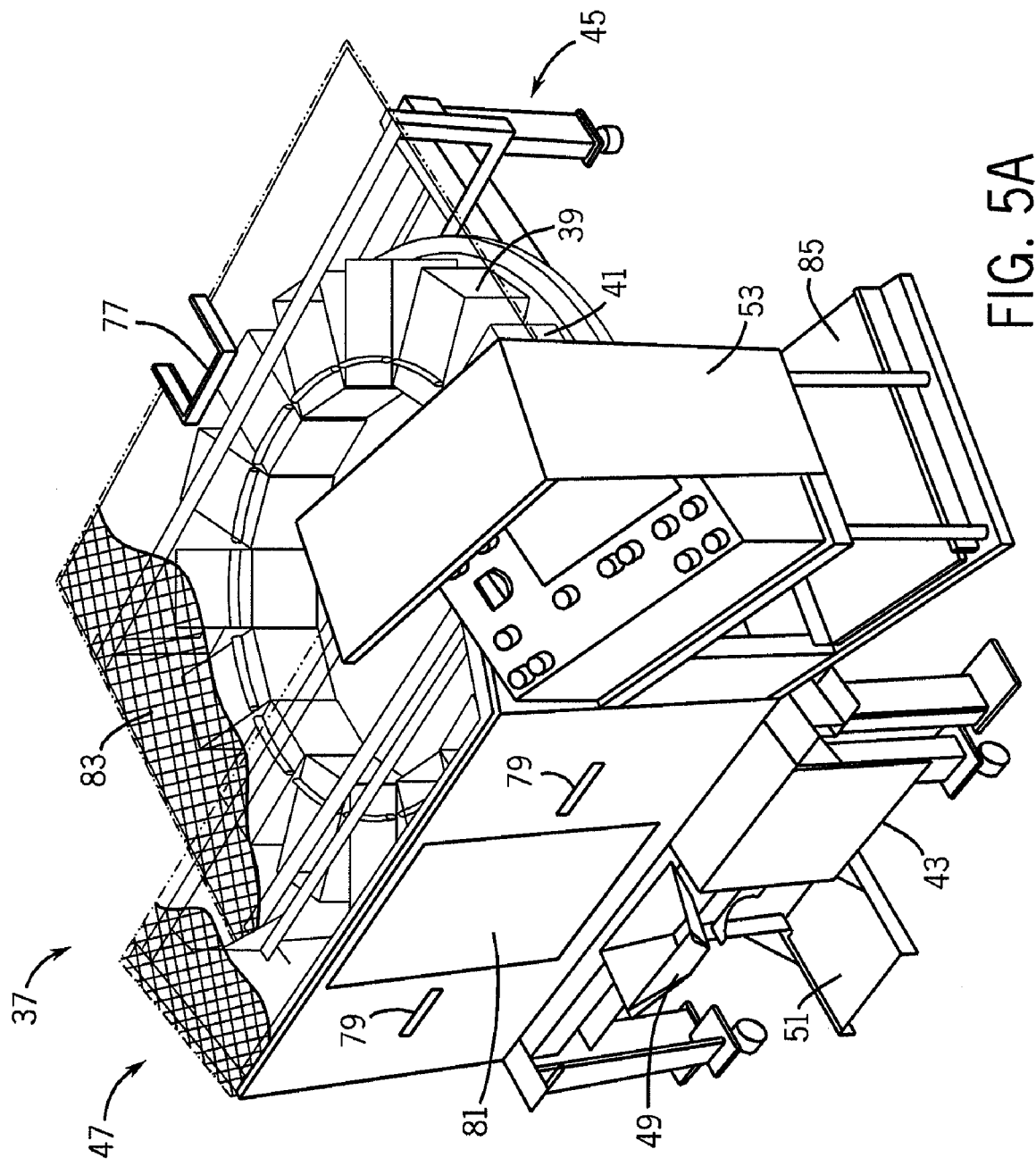
FIG. 5A is a perspective top view of the automated sample collection apparatus of FIG. 1 which illustrates the carousel assembly in combination with the access panel, control panel and funnel.
Figure 5B:
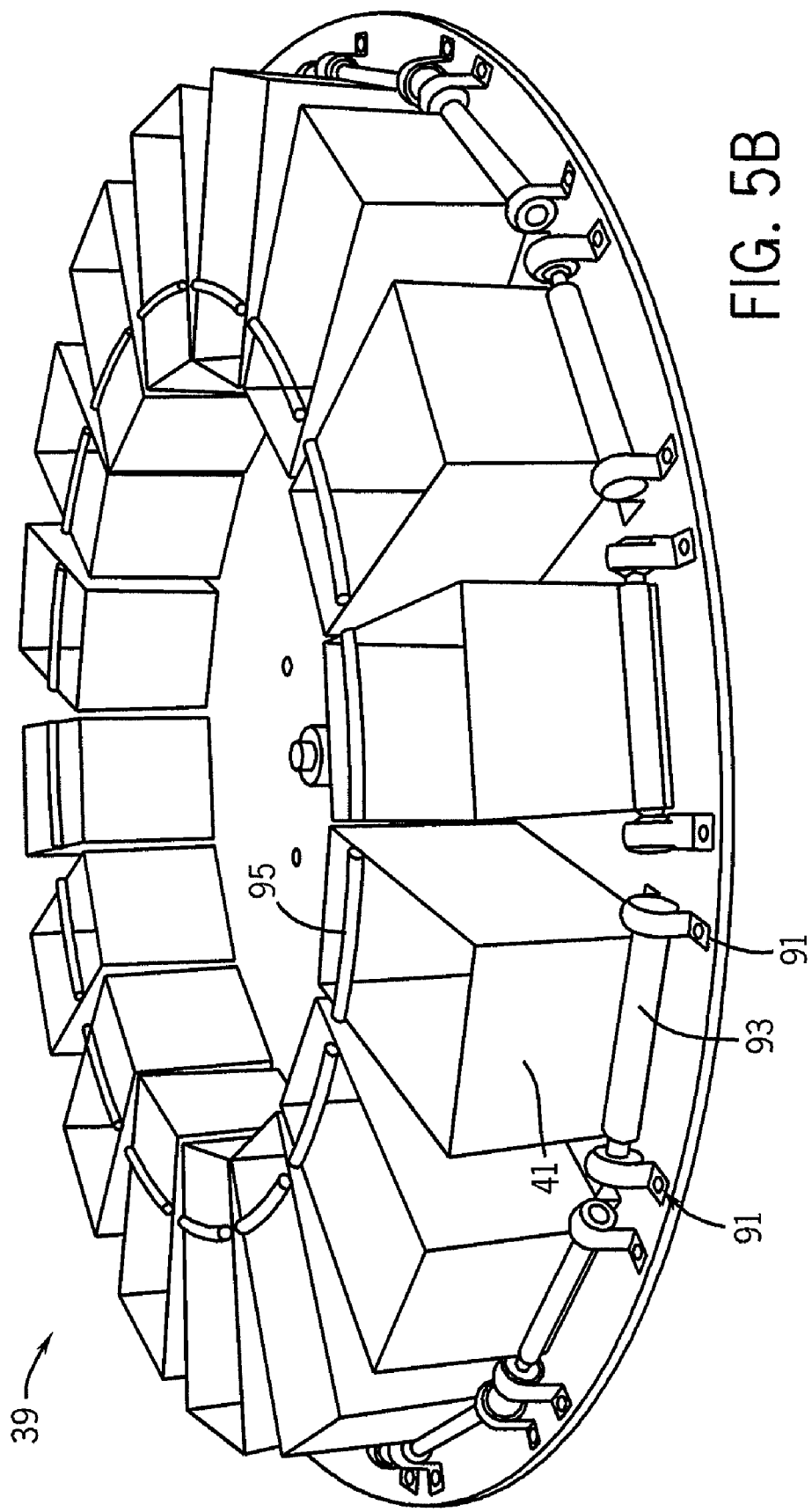
FIG. 5B is perspective top view of the carousel assembly of FIG. 5A which illustrates one embodiment of the positioning and attachment of the sorting containers to the top surface of the carousel and the pivot rods and handles of the sorting containers.

Referring now to FIGS. 3A and 3B in conjunction with FIG. 1, first chute 33 is located between and in open communication with collection container 31 and second chute 35 such that samples collected in the collection container are transferred to sorting containers 41 of FIGS. 5A and 5B through the second chute. First chute 33 is a pipe-like structure but in rectangular or trapezoidal shape with a first end positioned beneath the trapdoors of the collection container in such a manner that the samples in the chambers of the collection container fall into and through the chute. First chute 33 is equipped with door selectors 73 that can actuate the trapdoors of the collection container when either the chute or collection container is moved such that selectors 73 engage trapdoor release 26 (as shown in FIG. 2B). In one embodiment, the trapdoors are activated when the collection container is moved across the top, open end of the chute such that the trapdoor release engages the selector causing the door to open and the samples to spill out into the chute.

First chute 33 comprises top cover or panel 69 and rotation guard 67 that prevents samples from spilling out of the chute during their passage through the chute. Cover 69 is typically clear and removable to allow for inspection of the chute for clogs and to allow easy clearance of any clogs. In one embodiment the top cover is made of a clear or translucent plastic. The chute is not attached to second chute 35 which is a separate and distinct structure. However, at the time of sample transfer from the collection container to the sorting container, the first chute is brought into alignment with the second chute to form a passageway through which the samples can pass without spilling from the chutes. This alignment usually requires the movement of the first chute in a longitudinal direction on rails 21 toward the second chute which is stationary relative to both the first chute and carousel.

To assist the movement of the samples from collection container 31 to the second chute 35, first chute 33 is positioned in an inclined manner such that the samples emptying into the first chute from the collection container move by gravity into the second chute. To assist this movement, either or both of the first and second chutes can be equipped with one or more vibrators (not shown), typically attached to the underside of the chute.

Carousel assembly 37 shown in FIG. 5A includes nested inner and outer frames 43 and 45 respectively, which can be decoupled from each other to provide easy access to carousel 39 for maintenance and repair. Generally, inner frame 43 is mounted on movable wheels and outer frame 45 is mounted on stationary pads, and this nested arrangement allows the inner frame to be pulled away from the outer frame using a pair of recessed handles 79 located on a door assembly 47. Carousel assembly 37 includes carousel 39, access door assembly 47, funnel 49, storage container shelf 51, operator or control panel 53, and carousel protector screen 83.

With respect to carousel 39, it is used to receive and sort samples from the second chute and to store these samples temporarily until retrieved by an operator or other person. As shown in FIG. 5B, carousel 39 is essentially circular in shape and carries multiple sorting containers 41 positioned about the periphery of its top surface, each of which is affixed to top surface of the carousel by a pivot bar assembly comprising fasteners 91 and pivot bar 93. Although in the present embodiment carousel 39 is circular in shape, in other embodiments it can take on other generally circular shapes including for example, oval, hexagonal and octagonal. The carousel is rotated by an appropriately sized electric motor (not shown), typically a servo-electric motor, which is in a power transfer engagement with a gearbox (not shown) which is in a rotational engagement with a fastener (not shown) attached to the top surface of the carousel. Servo electric motors are electric motors equipped with any type of self-regulating feedback system or mechanism, e.g., a velocity and/or position feedback device, which affects mechanical motion for a specified distance. The sizing and placement of, and the connections between, the motor, gearbox and fastener are well within the skill of the ordinary artisan. Typically, carousel 39 is capable of moving in both clockwise and counter-clockwise directions.

Each of sorting containers 41 comprises a handle 95 by which the container can be rotated about the pivot bar so as to empty the contents of the container without removing the container from the carousel. Each of the sorting containers is essentially an open box (without a top cover) and sized to accept at least a full load of samples from one chamber of the collection container. Although shown as a box, the container can take essentially any shape that allows it to perform its functions of collection, holding and emptying.

Protection screen 83 is optional, and it is shaped and sized to provide a cover spaced apart from and over the open tops of the sorting containers positioned on the carousel. Typically the screen is made of a steel mesh or clear plastic that will safely support the weight of an operator while he or she inspects the carousel either while in operation or not, and to provide protection from something accidentally falling into one of the sorting containers. Notch 77 is simply a cutout in the protective screen that allows for the appropriate positioning of the second chute.

To retrieve samples from sorting containers 41, the operator positions the carousel so that the desired sorting container is directly behind safety door 81. A storage container (not shown, but typically a drum, bucket, plastic bag or the like, is positioned onto storage shelf 51 and below funnel 49. Access to the sorting containers is through the safety door which is secured with a magnetic lock. The door can be opened when the operator has disabled the lock, and this requires that the carousel is not in motion. Samples can be recovered from the sorting containers opening door 81, grabbing handle 95 of the sorting container that is positioned by the safety door, rotating the container so that the samples spill into the funnel and then into storage container, returning the container to its collection position on the carousel, and closing the safety door. A label can be prepared by a printer (not shown) located on printer shelf 85 of operator panel 53. The storage container with its contents can then be sent to a quality control laboratory for appropriate analysis. Carousel 39 can then resume motion to further collect, sort and store additional samples.

Operation of the automated sample collection apparatus is controlled by a software program designed to accomplish the orderly collection, sorting and storing of samples according to a sample regime or protocol. The apparatus requires minimal operator intervention. If the apparatus is sized to collect samples continuously over a 24 hour period, then operator time may be as little as once a day to collect a days worth of samples so as to empty the sorting containers for another's days activity.

This specification describes exemplary, representative, and non-limiting embodiments of the inventive arrangements. Accordingly, the scope of this invention is not limited to any of these embodiments. Rather, the details and features of these embodiments are disclosed as required. Thus, many changes and modifications—as apparent to those skilled in the art—are within the scope of the invention without departing from its scope.

What is claimed is:

1. An apparatus for collecting, sorting and storing samples, the apparatus comprising:
   A. A carousel comprising a plurality of sorting containers,
   B. Means for rotating the carousel,
   C. Means for transferring samples from a sampling station located apart from the carousel to the sorting containers, and
   D. Means for transferring samples from the sorting containers to storage containers located apart from the carousel.

2. The apparatus of claim 1 in which the carousel comprises top and bottom surfaces, each surface having inner and outer areas, and in which the sorting containers 41 are buckets spaced apart from one another on the outer area of the top surface of the carousel.

3. The apparatus of claim 2 in which the buckets are evenly spaced apart from one another.

4. The apparatus of claim 2 in which the means for transferring the samples from the sampling station to the sorting containers comprises a collection container and first and second chutes, the first chute located between and in open communication with the collection container and the second chute such that samples taken at the sampling station are collected in the collection container and transferred to the sorting containers through the first and then second chutes.

5. The apparatus of claim 4 in which the collection container (a) is attached to and moves with the sampling station, and (b) comprises (i) a housing defining a collection volume and having a closed bottom fitted with at least two trap doors and an open top, and (ii) at least one diverter plate with each plate dividing the collection volume into smaller volumes, one trap door defining at least a portion of each smaller volume.

6. The apparatus of claim 5 in which the collection container contains a single diverter plate dividing the collection volume into two smaller volumes of approximately equal size.

7. The apparatus of claim 4 in which the first chute further comprises (i) a vibrator for assisting the movement of samples through the first chute, and (ii) a clear panel through which the samples can be observed as they pass through the first chute.

8. The apparatus of claim 7 in which the first chute is affixed to a latitudinal set of rails that allow for the first chute to move in a longitudinal direction relative to the sample.

9. The apparatus of claim 8 in which the second chute (i) is not affixed to the first chute, (ii) comprises open entry and exit ends, and (iii) the exit end is positioned above the outer area of the carousel such that samples can pass from the first chute into the buckets.

10. The apparatus of claim 9 in which the sorting containers are affixed to the top surface of the carousel by a pivot rod assembly, the pivot rod assembly comprising (i) a pivot rod, and (ii) means for fastening the pivot rod to the top surface of the carousel such that the sorting container can pivot freely about pivot rod.

11. The apparatus of claim 10, the apparatus further comprising (i) an operator station, the operator station comprising an operator control panel, and (ii) an access door assembly separating the operator control panel from the carousel.

12. The apparatus of claim 11 in which the access door assembly is located opposite the second chute.

13. The apparatus of claim 12 in which the access door assembly comprises an access door panel comprising (i) a wall, (ii) a door, and (iii) a funnel located beneath the door such that when the door is open, samples from a sorting container can be transferred to a storage container by rotating the sorting container about the pivot rod so that the samples flow from the sorting container through the funnel into the storage container.

14. The apparatus of claim 11 in which the means for rotating the carousel comprises an electric motor in a power transfer engagement with a gear box in a rotational engagement with a fastening plate attached to the top surface of the carousel.

15. The apparatus of claim 14 in which the means for rotating the carousel further comprises control software.

16. A method for collecting, sorting and storing samples taken from multiple batches of copper cathode, the method comprising the steps of:
- A. Collecting samples from a first batch of copper cathode at a sampling station, and transferring the first samples to a first collection volume of a collection container comprising first and second collection volumes;
- B. Collecting samples from a second batch of copper cathode at a sampling station, and transferring the second samples to the second collection volume of the collection container;
- C. Transferring the first samples from the first collection volume of the collection container to a first sorting container through first and second chutes, the first sample moving through a first trap door in the collection container into the first and second chutes, and moving through the chutes due to at least one of (i) gravity, and (ii) vibration imparted to the first chute by a vibrator, the first sorting container pivotally affixed to a carousel;
- D. Rotating the carousel to position a second sorting container beneath the second chute to receive the second samples from the second chute, and then opening a trap door beneath the collection container such that the second samples in the second volume of the collection container exit the second volume and enter the first chute and move through the first and second chutes due to at least one of (i) gravity, and (ii) vibration imparted to the first chute by a vibrator, such that the second samples enter the second sorting container, the second sorting container pivotally affixed to the carousel;
- E. Rotating the carousel such that the first sorting container containing the first samples is positioned to a location removed from the second chute;
- F. Transferring the first samples from the first sorting container to a first storage container by pivotally rotating the first sorting container such that the first sample flows due to gravity from the first sorting container to the first storage container;
- G. Rotating the carousel such that the second sorting container containing the second samples is positioned to a location removed from the second chute; and
- H. Transferring the second samples from the second sorting container to a second storage container by pivotally rotating the second sorting container such that the second sample flows due to gravity from the second sorting container to the second storage container.

* * * * *